United States Patent
Hersh

(12) 
(10) Patent No.: US 6,242,010 B1
(45) Date of Patent: Jun. 5, 2001

(54) SYNERGISTIC ANTIOXIDANT COMPOSITIONS IN MANAGEMENT OF HEMORRHOIDS AND OTHER ANO-RECTAL INFLAMMATORY CONDITIONS

(75) Inventor: Theodore Hersh, Atlanta, GA (US)

(73) Assignee: Thione International, Inc., Atlanta, GA (US)

( * ) Notice: Subject to any disclaimer, the term of this patent is extended or adjusted under 35 U.S.C. 154(b) by 0 days.

(21) Appl. No.: 09/358,798

(22) Filed: Jul. 21, 1999

(51) Int. Cl.[7] .......................... A61K 33/04; A61K 35/78; A01N 37/44
(52) U.S. Cl. .......................... 424/702; 424/94.1; 424/400; 424/729; 424/DIG. 15; 514/882; 514/562; 514/937; 514/944; 514/966; 514/969
(58) Field of Search .................... 424/702, 400, 424/195.1, DIG. 15, 94.1, 729; 514/882, 966, 969, 937, 944, 562

(56) References Cited

U.S. PATENT DOCUMENTS

| | | | | |
|---|---|---|---|---|
| 5,268,455 | * | 12/1993 | Cianciolo | 530/404 |
| 5,667,791 | * | 9/1997 | Hersh et al. | 424/401 |
| 5,827,886 | * | 10/1998 | Hersh | 514/562 |
| 5,906,811 | * | 5/1999 | Hersh | 424/54 |
| 5,939,394 | * | 8/1999 | Fleming et al. | 514/23 |

OTHER PUBLICATIONS

Buckley et al. Proc. Natl. Acad. Sci. USA, vol. 82, pp. 7340–7344, Nov. 1985.*
PCT Search Report, International Application No. PCT/US00/20039, Filing Date: Jul. 21, 2000, 5 pages.

* cited by examiner

*Primary Examiner*—Christopher R. Tate
(74) *Attorney, Agent, or Firm*—Malcolm B. Wittenberg

(57) ABSTRACT

Compositions for remediating ano-rectal inflammatory processes, hemorrhoidal syndromes and ano-rectal wounds. The composition includes the synergistic combination of reduced glutathione and selenium as a selenoamino acid in a suitable carrier for topical applications.

12 Claims, No Drawings

SYNERGISTIC ANTIOXIDANT COMPOSITIONS IN MANAGEMENT OF HEMORRHOIDS AND OTHER ANO-RECTAL INFLAMMATORY CONDITIONS

TECHNICAL FIELD OF THE INVENTION

The present invention deals with compositions for ano-rectal inflammatory processes, hemorrhoidal syndromes, pruritus ani and ano-rectal wounds comprising a complex of synergistic antioxidants, including enzymatic co-factors, thiol and selenium compounds, zinc salts and cellular growth factors to decrease the local inflammatory response, abolish symptoms, and to promote wound healing and surgical repairs, such as post-hemorrhoidectomies, fistulectomies, and fissurectomies. These active ingredients will be administered using topical ano-genital and intra-rectal preparations, most particularly, ointments, salves, lotions, creams, patches, aerosols, sprays and others and as suppositories and foams for internal hemorrhoids and rectal inflammatory conditions so that the antioxidants neutralize and scavenge the free radicals generated in ano-rectal diseases and local wounds thereby reducing the pain, inflammation, swelling, itching, and tenderness in these anatomical parts, and together with other optional ingredients promote repair and healing.

BACKGROUND OF THE INVENTION

Hemorrhoids are one of man's main afflictions. *Homo sapiens* pays this price, hemorrhoids, for its primate ancestor, *Pithecanthropus erectus*, stood up in contrast to his other non-human primates and other mammalian species wherein hemorrhoids do not occur. Hemorrhoidal syndromes are a condition with great morbidity but fortunately minimal mortality, albeit frequent bothersome symptoms and complications.

"Hemorrhoids", often referred to as "piles" or "almorranas" by Hispanics, are truly enlarged veins in the area around the anus, anatomically known as the hemorrhoidal plexi. These veins constitute the external and the internal hemorrhoids. The hemorrhoidal plexus is formed by the anastomosis of two distinct venous systems; the systemic via the inferior vena cava and the hepatic via the portal vein. Whichever venous system has an increase in its pressure, permanent or intermittent, will cause varicose dilation of the hemorrhoidal veins. The most common etiology for the former venous system is right sided congestive heart failure while for the latter, is caused by cirrhosis of the liver with portal hypertension. Unfortunately, both types of clinical syndromes are commonly associated with hemorrhoidal complications often affecting these chronically, very ill patients. However, hemorrhoidal syndromes are very common even in the absence of the aforementioned venous hypertension entities.

Signs and symptoms of the hemorrhoidal syndrome are variable and result from the "swollen" (enlarged) hemorrhoidal veins in and around the anus and rectum, respectively labeled external and internal hemorrhoidal syndromes. Although the presence of these dilated veins may be asymptomatic, many patients complain of passing bright red blood covering the stool, or noticing blood on the toilet paper or toilet bowl. Internal hemorrhoids may protrude through the anus becoming irritated and painful and pathologically having a severe cellular inflammatory response in the contiguous tissues. External hemorrhoids may likewise include an inflammatory response in the anal mucosa and may include a painful selling or hard lump, particularly with a thrombus (clot), around the anus. Excessive straining, rubbing or cleaning around the anus may cause further irritation and inflammation with generation of free radical species to further the painful symptoms, with consequent bleeding, itching, and draining mucus, a true curse of the inflammation and distention of these veins.

Although hemorrhoidal symptoms may subside within a few days, many cases are associated with local and rectal complications, including fissures, fistulae, abscesses or irritation and itching (so called pruritus ani). The inflammatory reactions are chronic, indolent and infected. Not infrequently these patients succumb to one or another of the available surgical treatments. Surgical therapies include electrical or coagulation laser or infrared photocoagulation to "burn" the hemorrhoids; rubber band ligation to cut off circulation; sclerotherapy to shrink these veins by injecting agents that "scar" these veins or by surgical removal, hemorrhoidectomy. All these primitive and advanced methods may be averted by proper preventive measures and therapeutic applications such as reparative sitz baths and the use of local ointments, creams, lotions, patches and suppositories with both therapeutic anti-inflammatory agents, vaso-constrictors, and synergistic anti-oxidants as in this patent application to reduce inflammation, swelling and free radical species damage to the putative ano-rectal tissues and hemorrhoidal veins.

In addition to the hemorrhoidal syndromes, there are other important anal inflammatory conditions. Inflammations of the anal conduit (canal) are variously called anusitis, cryptitis and papillitis, usually caused by alterations in the rhythm of defecation, that is, alternating periods of constipation and diarrhea, the latter with its variations in stool pH and fecal chemical constituents, such as the presence of active digestive enzymes. Alterations in fecal micro-flora, gastrointestinal infections and parasitic infestations, particularly pinworm, are responsible for anal inflammation, whereby the antioxidant complex of the present invention in appropriate delivery vehicles may be an adjunct to therapy of ano-rectal diseases.

Another common and very painful condition is anal fissure, which is a linear ulcerating lesion in the anal canal. This is purportedly tabulated as the most painful anal inflammatory condition. Pruritus ani is another common syndrome accompanied by intractable itching and local inflammation resulting from hemorrhoids, local infections, dermatologic diseases and pinworm disease among the most common. The intense itching leads to excoriations, ulcerations and complicating inflammation with secondary infections.

Other causes of ano-rectal inflammation are sexually transmitted diseases and perianal infections and abscesses. The later often originate from a suppurative cryptitis, or from a fissure. Fistula-in-ano may result from a perianal abscess and is a chronic, indolent and painful condition. Inflammation is most prominent and requires antibiotics and drainage with local care including topical analgesics. The present antioxidant preparations would be an important adjunct in the symptomatic and reparative management of these ano-rectal inflammations.

There are a number of patents which have been issued for compositions and methods of treating hemorrhoids and related ano-rectal wounds. Topical formulations not only treat hemorrhoidal pain but also sphincter spasm and related symptoms. Gallina in U.S. Pat. No. 5,234,914 dated Aug. 10, 1993, taught a method of applying to ano-rectal tissues and to hemorrhoids a composition which included hyaluronic acid or its salts in amounts ranging from 0.1 to 10% by weight, in acceptable carriers. The uses of hyaluronic acid included its anti-inflammatory and wound healing properties for ano-rectal conditions and diseases, Packman and Oskman described the use of hemorrhoidal compositions containing disaccharide polysulfate-aluminum compounds, like sucralfate in U.S. Pat. No. 5,196,405, Mar. 23, 1993. This method of alleviating hemorrhoidal symptoms included sucralfate alone or in combination with antibiotics, anti-fungal agents or local anesthetics in an attempt to ameliorate ano-rectal symptoms and heal the putative wounds. Compositions could also include anti-inflammatory agents, steroids, and/or vaso-constrictors, causing a complex matrix to be formed between the wound and the sucralfate in order to promote a prolonged adhesion of the preparation to the affected tissue.

U.S. Pat. No. 4,761,285, dated Aug. 2, 1988, taught various compositions for the relief of hemorrhoidal symptoms and the treatment of hemorrhoids. It taught a preparation comprising leptandra's culver root, chick peas, and grape seeds. The latter are now known to contain proanthocynidins, antioxidants which are also present in pine bark extracts. These investigators enhanced their topical preparation with honey, cinnamon and oils. Okumura and associates more recently disclosed the use of prostaglandins in the therapy of hemorrhoids and wounds in U.S. Pat. No. 5,852,050 dated Dec. 22, 1998, which is herein incorporated by reference. Stable prostaglandins, as Geraprost, are used as oral or topical preparations because these prostaglandins improve peripheral blood circulation while inhibiting thrombus formation through a decrease in platelet aggregation.

U.S. Pat. No. 4,784,842 dated Nov. 15, 1988, disclosed a composition for treatment of abrasions and cuts comprising a terpene and a vitamin E compound. The preparation purportedly facilitated healing and reduced swelling, bleeding and pain by applying the mixture to the affected external area. Also taught are that the treatment mixture could be administered by aerosols for spraying. Similarly, as in the present invention, a suitable complex of antioxidants and minerals for adjuvant management of ano-rectal diseases may be administered by pump or mist spray packaging or by pressurized aerosols, according to the guidelines for propellants issued by the FDA.

In U.S. Pat. No. 4,613,498 dated Sep. 23, 1986, Crosby disclosed an external hemorrhoid medication as a petroleum jelly ointment. The reference taught a powdered mixture of alum, quinine sulfate and aspirin be applied topically to the affected area. Anderson, in U.S. Pat. No. 4,162,866 dated Mar. 11, 1980, taught an anorectal medication comprising glycerides and fragments of the ripe berry of the plant solanum carolinense (horse nettle). The reference also included sulfur, ammonium alum and turpentine. Earlier, Urbin, in U.S. Pat. No. RE28,O dated May 14, 1974 disclosed the use of oxidase enzymes to treat hemorrhoids, by destroying the amines formed by the fecal microflora in the colon.

U.S. Pat. No. 5,595,753, dated Jan. 21, 1997, taught the use of L-arginine for topical formulations for treating hemorrhoidal pain and sphincteric muscle spasm in gastrointestinal tract. Inflammation of the anal mucosa and hemorrhoids cause spasms of the internal anal sphincter with consequent ano-rectal pain. The pain associated with hemorrhoids is due primarily to the adjacent inflammatory reaction. Nitric oxide (NO) is a known modulator of sphincter tone, to which the amino acid L-arginine acts as a competitive inhibitor of compounds that block the action of NO production. Thus, L-arginine's use as taught in the '753 patent in topical preparations, alleviates anal pain by decreasing internal sphincter tone and thereby abolishing sphincter spasm. This amino acid does not participate as an antioxidant in the amelioration of the local inflammatory response, as proposed by the compositions of the present patent application.

Suppositories consisting of tissue respiratory factor as the active ingredient are known. Analgesic and anti-inflammatory compositions for topical applications were also disclosed by Reller and Kretschmar in U.S. Pat. No. 4,199,576, Apr. 22, 1980. The reference taught a number of salicylic acid derivatives as useful non-irritating topical anti-inflammatory agents which, like aspirin, are inhibitors of prostaglandin synthesis. Like the latter, histamine, serotonin, and the kinins are mediators of inflammation but with these the prostaglandins are continuously biosynthesized and released from the cells at the site of inflammation. Since prostaglandins have a longer effect in situ, it is suggested by the present invention that it is vital to decrease inflammation's free radical tissue damage with topical antioxidants plus the known anti-inflammatory agents like the salicylates, steroids and other derivatives so well known in the art of this industry.

Another common brand of hemorrhoidal suppositories and ointment is marketed under the trade name of Anusol. The composition includes pramoxine hydrochloride and zinc oxide, with the former containing bismuth subgallate and bismuth resorcin. Some preparations of Anusol also include hydrocortisone 1%. Their stated indications are for itching, burning and soreness of hemorrhoids and other minor ano-rectal discomfort and irritation.

There are many other over the counter ano-rectal products, but none contain the antioxidant complex of the present invention. They contain other topically beneficial ingredients for ano-rectal conditions, each with designated therapeutic goals, for example, vaso-constrictors and analgesics to decrease pain, itching, swelling, soreness or to diminish the size of the hemorrhoids or its bleeding complications. Some examples of these OTC products include americaine, balneol, calmol-y, cortex rectal itch ointment, diothane, epinephricaine, gentzy and tucks wipes, proctofoam, nupercainal, Vaseline, wyanoids, and many others. These all conform to Code of Federal Regulations 45-33576, dated May 22, 1980.

Local anesthetics such as benzocaine and related caines may be added to ameliorate discomfort and pain, and tissue respiratory factor, which also diminishes discomfort and stimulates fibroblast's metabolic functions to deposit collagen. As noted below, to enhance the healing of muco-cutaneous lesions, the present invention may also optionally add epidermal growth factor and/or other cellular growth factors and hormones, which stimulate epithelial cell growth, vital in the repair process to accelerate wound healing.

Various patents have been issued for both tissue protection and for repair of wounds. These compositions may also be used, but are not limited, to ano-rectal inflammatory wounds, surgeries and burns. Pickart in U.S. Pat. No. 5,554,375, dated Sep. 10, 1996, which is herein incorporated by reference, disclosed compositions for protecting irritated or damaged skin from further oxidative and biochemical damage, thereby allowing the repair process to progress. Many of these compositions accelerate the rate of healing of wounds and burns. Pickart taught for these uses complexes of peptone digests of various proteins, like soybean protein, with salts of copper, tin, and indium while the '090 patent of Okumura et al. disclosed the benefits of vasoconstrictors and inhibitors of clot formation with stable prostaglandins.

In summary, the main pharmacologic ingredients in these ano-rectal compositions include moisturizers, local anesthetics, such as benzocaine, dibucaine, pramoxine, lidocaine, tetracaine and others; vaso-constrictors such as ephedrine and epinephrine; nitrates to reduce anal sphincter spasm; protectants, such as aluminum hydroxide gel, calamine, cocoa butter, cod liver oil, glycerin, lanolin, mineral oil and others; and wound healing agents, as vitamins A and D, and zinc compounds, as noted. Astringents, antiseptics, keratolytic agents and anti-cholinergics may also be part of these therapeutic compositions.

Despite the impressive pharmacologic activity directed to reducing pain and promoting healing of ano-rectal conditions, no one has recognized the benefits that antioxidants can play and particularly, the benefits that can be derived from using the synergistic antioxidant complex of the present invention.

It is thus an object of the present invention to provide various compositions and methods of employing the present compositions for ameliorating and treating inflammatory ano-rectal conditions and hemorrhoidal syndromes. The preparations are designed to improve both signs and symptoms of ano-rectal diseases and aid in the repair processes of the aforementioned to avoid development of the distressing and debilitating complications of ano-rectal diseases and hemorrhoids.

These and further objects will be more readily appreciated when considering the following disclosure and appended claims.

SUMMARY OF THE INVENTION

The present invention deals with a composition and method of employing the composition for ameliorating inflammatory symptoms of hemorrhoids and other ano-rectal conditions.

The composition includes the reduced form of glutathione with a selenium source as a co-factor of glutathione peroxidase as antioxidants. The composition may be topically applied as a lotion, cream, ointment, gel, spray or emulsion or by its inclusion into a suppository vehicle or foam together with further wound healing ingredients, anti-inflammatories and analgesics as discussed below.

DETAILED DESCRIPTION OF PATENT

In the preferred embodiment of this invention, the locally applied compositions of the synergistic antioxidant complex whether in suppositories, enemas, sprays, ointments, creams, salves, lotions, patches, foams or other carriers will be adjuncts to therapy of acute and chronic ano-rectal inflammatory conditions. The intent of this invention is to provide a composition to neutralize and scavenge free radical species generated in ano-rectal tissues including but not limited to classic internal or external hemorrhoidal syndromes, with or without complications such as fistula-in-ano, rectal fissures, pruritus ani, proctitis and others as already noted including post-surgical wounds. A further embodiment of this invention is to provide the antioxidant complex with wound healing preparations including but not limited to zinc salts, like zinc oxide and zinc pyrithione, and epidermal growth factors, as well as hyaluronic acid for treatment also of ano-rectal wounds and inflammation such as fistulae, fissures, proctitis, bleeding hemorrhoids, infections, immune deficiencies with local complications including Kaposi's sarcoma and others.

It is also a preferred embodiment of this invention to provide the synergistic antioxidant complex with anti-inflammatory medicaments and analgesics not only to reduce the free radical and inflammatory cell response to the putative ano-rectal condition(s) but also to reduce the most distressful ano-rectal symptoms of pain, tenderness, pruritus (itching), swelling, bleeding, anal and genital discomforts and soreness. Another embodiment is to provide these compositions as adjuncts of therapy to the sitz baths for management of internal and external hemorrhoids and for the reduction in swelling, inflammation, bleeding, and size of the hemorrhoids and other anal and genital diseases and infections and post-surgical interventions.

Cells subjected to oxidative stress may severely affect cellular function and cause damage to membrane lipids, to proteins, to cytoskeletal structures and to DNA. Free radical damage to DNA has been measured as formation of single-strand breaks, double-strand breaks and chromosomal aberrations. Cells exposed to ionizing radiation and cigarette smoke have also been demonstrated to have an increased intracellular DNA damage related to free radicals, a precursor to the development of mutations and malignancies.

Marcrophage cells and neutrophils have their phagocytic activity associated with the so-called "respiratory burst" reaction, which is dependent on plasma membrane NADPH oxidase activity. The resulting oxygen radicals may then be transferred to $H_2O_2$ by superoxide dismutase, an antioxidant present in the compositions of this patent application.

The muco-cutaneous repair processes are common to inflammation, infections, surgical repairs and dermatologic conditions, as aforementioned. Ano-rectal and cutaneous tissues so exposed to injury react so that water molecules contained within cells are altered and lipids of membranes or extracelluar tissues are also injured resulting in the formation of a number of noxious free radicals. This is known as the process of lipid peroxidation and affects ano-rectal diseases.

During the process of phagocytosis by polymorphonuclear leucocytes, an increased consumption of oxygen occurs. This "respiratory burst" generates superoxide radicals, hydrogen peroxide, the hydroxyl radical and hypochlorous acid. Hydrogen peroxide is derived from the free oxygen species by a process called dismutation. In muco-cutaneous tissues, oxygen radicals are also made by fibroblasts. Following wounds or burns, there is an increased level of the enzyme xanthine oxidase in these tissues, which also generate free oxygen radicals.

Teleologically, the skin's surface has a well developed endogenous antioxidant defense system to combat free radicals including the enzymes superoxide dismutase, catalase, selenium dependent glutathione peroxidase and the ubiquitous thiol tripeptide, glutathione, in its reduced form. Also present are the nutritionally provided vitamins C and E, including the hydrophilic antioxidant ascorbic acid and the lipophilic antioxidant alpha tocopherol, respectively.

Acute damage to these tissues results in muco-cutaneous inflammatory response. Clinical symptoms include discomfort, pain, tenderness, itching, while local signs include erythema and edema. Inflammation associated with itching results in scratching, which further traumatizes these tissues, particularly in pruritus ani. This trauma causes bleeding into the affected tissues, such that hemoglobin is released from the red blood cells. When the hemoglobin is exposed to the hydrogen peroxide generated from neutrophils and xanthine oxidase in inflamed tissues, there is hemoglobin degradation and consequent release of catalytic iron ions and toxic free heme which are themselves capable of initiating or aggravating lipid peroxidation. These events in damaged tissues increase the inflammatory response while the consequent excoriations from the pruritus make these affected surfaces more likely to become infected by secondary bacterial contamination.

Antioxidant enzymes exist in ano-rectal tissues including superoxide dismutase (SOD), which converts superoxide to hydrogen peroxide and catalase which reduces hydrogen peroxide to water. This reaction may also be catalyzed by selenium as a cofactor to the enzyme glutathione peroxidase using reduced glutathione (GSH) as a substrate. GSH-peroxidase may also reduce lipid peroxides to the corresponding alcohols, also using GSH.

Glutathione, a sulphur containing tripeptide (L-gamma-glutamyl-cysteinyl) is the most abundant non-protein thiol in mammalian cells and is recognized as the primordial antioxidant. Glutathione, in its reduced form, known as GSH, also acts as a substrate for the enzymes GSH-S transferases and GSH peroxidases (with selenium cofactor) that both catalyze the reactions for the detoxification of xenobiotic compounds and for the antioxidation of reactive oxygen species and other free radical species.

GSH synthesis takes place in two steps:
(1) An initial rate limiting step catalyzed by gamma glutamyl cysteine synthetase to form gamma glutamylcysteine.
(2) Glutathione synthetase catalyzes the reaction between glycine and glutamylcysteine to form GSH.

Intracellular stability is conferred to GSH by the gamma glutamyl bond's resistance to intracellular peptidases. This bond may be cleaved by gamma glutamyl transpeptidase which is usually located on the external surface of cell membranes. Its activity is high in the kidney, where GSH is subject to renal clearance by tubular cells. This transpeptidation reaction, results in urine excretion or retransport to plasma of the constituent amino acids, glutamine, cysteine, and glycine. In this pool, along with nutritionally derived amino acids from digestion and small bowel absorption, these amino acids are available to the liver for GSH synthesis. The liver and lung also export GSH in its oxidized form denoted as GSSG, which is produced when peroxides are detoxified by GSH peroxidase. GSSG is recycled back to the reduced form, GSH, by the cellular enzyme glutathione reductase in a reaction utilizing NADPH.

The ubiquitous glutathione plays a vital function in maintaining the integrity of the reactive oxygen species-free radical sensitive cellular components. This is accomplished through its direct role as an antioxidant, in its reduced (GSH) form, as well as a cofactor as aforementioned. In cells, GSH concentrations for antioxidant activity are maintained in equilibrium by the enzyme glutathione reductase. Under states of GSH depletion, including malnutrition and severe oxidative stress, cells may then become injured from excess free radical damage and die.

Other non-enzymatic molecules playing an antioxidant role include the ascorbates (vitamin C) which, as free radical scavengers, also react to oxidized glutathione (GSSG) and reduce it to a GSH. Also, in the lipid membrane of the cells, the hydrophobic alpha-tocopherols (vitamin E) act synegistically with vitamin C to inhibit lipid peroxidation by actively scavenging lipid peroxides and other radicals. The enzyme glutathione reductase abundant in all cells is the principal mechanism to reduce glutathione to its active form.

Selenium functions as an anti-oxidant and by its role as a cofactor for glutathione peroxidase, a group of water soluble enzymes which also catalyze the destruction of both aqueous and membrane-bound hydroperoxides. In dietary selenium deficiency, these enzyme levels are markedly decreased resulting in severe free radical damage to the tissues so involved. The other related anti-oxidant systems cannot make up for depressed local activity of selenium and selenium dependent enzymes. Selenium deficiency also occurs after such injuries as burns and needs to be supplemented in these states. Thus, the importance of providing selenium in these topical anti-oxidant preparations, as well as ascertaining adequate dietary supplements. Indeed, recent epidemiologic studies have shown that supplemental selenium at a dose of 200 mcgm daily, may reduce both the incidence of and the mortality from carcinomas of various sites.

Selenium has also been shown to affect the immune system. Selenium supplementation as 70% selenomethionine in patients with psoriasis with normal pretreatment selenium blood levels showed an increase in blood levels of 40% post treatment. A statistically significant increase in the number of CD4 +T-cells was noted in the reticular dermis of the psoriatic lesions. In other studies in human subjects, topical selenomethionine was investigated for its ability to reduce the degree of acute inflammatory damage to the skin by ultraviolet radiation. The effects demonstrated by topical selenomethionine in human volunteers on measurement of minimal erythema dose, suggests that the protection to ultraviolet irradiation by this compound is not simply a sunscreen effect. The selenomethionine is absorbed percutaneously and acts locally as a free radical scavenger.

Further, glutathione and selenium act synergistically in vivo as they are both constituents of the same enzymatic system. GSH serves as a specific donor substrate while selenium, provided from alimentary sources or locally from topically applied preparations of selenoamino acids, selenium yeast extracts or selenoamino acid chelates, provides the prosthetic group of GSH peroxiclase. The glutathione and selenium antioxidant functions are intrinsically related since by keeping a peroxidase in action. GSH and selenium contribute to the removal of the dismutation product of free oxygen radicals, namely, hydrogen peroxide. In a broad sense, GSH and selenium modulate free radical chains initiated or sustained by hydroperoxides. Thus, their synergistic value in these antioxidant topical compositions.

The present invention further contemplates the use of additional optional expedients, for example, superoxide dismutase (SOD). SOD is a ubiquitous cellular enzyme whose main function is in protecting cells against oxidative stress. Superoxide dismutases are a family of cytosolic metalloenzymes which specifically remove free oxygen radicals. There are three distinct forms of SOD, namely, CUZN SOD, MN SOD and extracellular SOD (EC-SOD) which is a copper enzyme located on endothelial cell surfaces. The differences in the SODs are in their aminoacid sequences as well as in the location at their active sites of the transition metals. It is hypothesized that the enzyme SOD, along with glutathione peroxidase and its selenium cofactor, are effective preventive antioxidants because they eliminate molecules involved in the initiation of free radical chain reactions. SOD also protects intracellular reduced glutathione against radical mediated chain oxidation as the combination of SOD and reduced glutathione prevents redox cycling reactions.

It is also contemplated that, as a further optional expedient that the present composition contain from approximately 0.01% to 10.0% Japanese green tea by weight based upon the weight of the other active ingredients. Chemically, extracts of Japanese green tea have been analyzed and characterized. Active ingredients include caffeine, theobromine, theophylline and xanthines which, together, have been shown to reduce irritation of the skin, including that caused by various alpha hydroxy acids and other ingredients in cosmetics, thus making green tea an important supplement to topical cosmetic and dermatological preparations. Green tea also contains potent polyphenols, catechin compounds which effectively act as antioxidant agents to scavenge for free radicals. The main catechin constituent of green tea is (-)epigallocatechingallate (EGCG). It has also been shown that EGCG inhibits hydrogen peroxide formation by human leukocytes, the first cell in the inflammatory cellular response to injury and infection. EGCG is of value to function synergistically as an exogenous antioxidant in these topical preparations with the active ingredients composed of endogenous antioxidants.

In a preferred embodiment, the compositions of the present inventions may be enhanced by the addition of zinc salts, including zinc pyrithione. Zinc may function by its healing properties on wounds, particularly as zinc oxide, and also to render the present preparations odorless, presumably by removing races of hydrogen sulfide, which could emanate from the sulfur groups used in these preparations. Zinc may also be administered as one of the trace metals prepared in yeast extracts as mineral (zinc) glycopeptides. Zinc pyrithione also possesses antioxidant activity.

Compositions preferably comprise from about 0.001% to about 8% by weight of a zinc salt, preferably from about 0.01% to about 4%, more preferably still from about 0.1% to about 0.5%, and 0.005 to 0.25 only for the zinc pyrithione.

Zinc, the second most abundant trace metal in the human body and present in all living cells and body secretions, was identified as a trace metal by Ravlin in 1869. For over 3,000 years, zinc in the form of zinc oxide or calamine, has been used in the treatment of wounds. Zinc is still used in castor oil and as zinc oxide for treatment of "diaper rash" and in a vast number of zincated bandages, dressings and creams.

It has more recently been shown that zinc metalloenzymes in the skin have a prominent role in the reconstruction of the wound matrix. Zinc, along with copper is necessary for cross-linking of collagen fibers in the repair process. Although zinc probably plays a role in all stages of healing, zinc concentration increases at the margins of the wound during the formation of granulation tissue, re-epithelialization and normalizing periods. The concentrations of zinc in the margins of the wound during repair are 15–20% higher than in contiguous intact skin and are provided from zinc in blood. Since zinc thus is of value in the healing process as shown in experimental animals and in clinical studies with zinc oxide, the addition of zinc as an ingredient to these ano-rectal preparations will promote healing and enhance the repair process.

Puradelli in U.S. Pat. No. 4,910,222, dated Mar. 20, 1990, but abandoned in 1994 and herein incorporated disclosed the use of D/L cysteine or cysteine derivatives. Cysteine has a bronchial liquefying and expectorating property. The rectal route in posologic units of 10.0 to 100.0 was one of the means of administering the amino acid. No mention herein is made of cysteine as an antioxidant or component of glutathione and its local application to ano-rectal inflammation and hemorrhoidal disease.

In the present formulations using antioxidants and anti-inflammatory compounds, one or more cell growth stimulating compounds in suitable amounts effective for stimulating the growth of cells which encompass or surround the wound and are injured and/or are responsible for healing wounds may be optionally incorporated in the preparations of the present compositions, including but not limited to suppositories, ointments, salves, creams, lotions, gels, patches, sprays or other carrier vehicles. Skin cellular reparative functions of ano-rectal and perineal diseases and wounds, which include post-surgical repairs and hemorrhoidectomies are mentioned in the list of therapies as examples.

Also useful herein is a component known as Tissue Respiratory Factor (TRF). TRF is a live yeast cell derivative which has been used in over the counter pharmaceutical preparations since the 1940's and more recently as an ingredient in cosmetics. It is commercially available and purported to be a powerful internal moisturizer which refreshes dry and infirm skin. TRF was first used as an anti-hemorrhoidal product (Preparation H, Whitehall Laboratories). Because TRF is prepared from live yeast cells derivatives, additional trace quantities of coenzymes, vitamins, amino acids and minerals, characteristic of yeast, are available in these factors, which enhance the therapeutic capabilities of TRF in these pharmaceutic/cosmetic preparations. TRF has been shown to promote wound healing through its ability to increase fibroblast synthesis of collagen and elastin fibers resulting in smoothing of the skin. TRF's moisturizing effect is accomplished by increasing uptake of moisture by nascent protein and increasing oxygen utilization in the skin. TRF has been used in the treatment of sunburned skin and has been preferred for decreasing pain and discomfort of damaged skin when compared to the local anesthetic benzocaine. Thus, TRF, as other growth factors, may be used in combination to these proposed synergistic antioxidant preparations in ano-rectal inflammatory processes and in local wound repair, such as anal fistula and fissures and surgically created wounds.

"Cell growth stimulating compounds or factors" have been described as natural or exogenous compounds which have a stimulating effect on the elaboration and growth of specific cell lines. Specifically, in regard to promoting epidermal growth, such as in muco-cutaneous tissue repair from inflammation or wound healing, various factors have been identified.

As a further optional expedient is the use of epidermal growth factor (EGF), an endogenous substance for the development and maintenance of the epidermis and dermis. EGF is a protein that catalyzes the cutaneous healing process by promoting epidermal and epithelial cells to divide and grow. It induces mitoses, so that these tissues constantly produce and use EGF, particularly when these tissues are damaged, such as in inflammatory reactions and after surgery for healing. When applied topically, EGF generates and replaces epithelial cells. EGF also promotes synthesis of proteins, accumulation of collagen and formation of blood vessels. The antioxidants protect and repair damaged ano-rectal tissues from free radicals while the growth factors to be used in these combinations will promote cell renewal and thus ensue in repair of affected tissues.

Epidermal growth factor is a 53 amino acid polypeptide which stimulates messenger RNA, DNA and protein synthesis. After disease or injury, residual epithelial cells proliferate in an organized fashion to regenerate. Superficial wounds which do not result in total skin loss but retain at least a portion of the dermal layer, heal primarily by this process of epidermal regeneration. Epidermal growth factor induces replacement of cells by inducing mitosis. Many experiments, animal and human studies, have positively shown the beneficial effect of EGF in the process of wound repair.

Thiol rich yeast extracts and wheat extracts, both commercially available, also provide glutathione peroxidase and the sulphur groups to promote glutathione synthesis and enhance the glutathione pathways. These extracts are used in concentrations ranging from 0.5% to 8%, most typically 3.0 to 5.0% and usually at 1.0% to 2.5% by weight.

Additional therapeutic medicaments may be added to these formulations depending on the specific indication for each preparation and application. These additives may be selected from the following not uncommonly used medications in suppositories and ano-rectal compositions, including, but riot limited to, anesthetics, corticosteroids, anti-inflammatories, wound healing salts, vasoconstrictors, lubricants, astringents, antiseptics, anti-microbials and others known in these pharmaceutical arenas.

The present complex of synergistic antioxidants with minerals may be formulated as a solid (suppositories), gel, cream, lotion, paste, salve, spray or ointment, depending on the base ingredients and the amounts used, as are known in the state of the art in this industry.

EXAMPLE I

RECTAL CREAM

A rectal cream can be prepared with the active ingredients described above. The cream has a base of stearic acid, cetyl alcohol, isopropyl palmitate, polyoxyl-40 stearate, propylene glycol, triethanolamine, sorbic acid (0.1%), lauryl sulfate and water. Hydrocortisone at 1.0% to 2.5% depending on the concentration desired, may be added, as "H-C" preparations commonly known in over the counter ano-rectal preparations or by prescription. Topical corticosteroids enhance the anti-inflammatory properties of the antioxidant complex and are also known to be anti-pruritic and vasoconstrictive agents.

EXAMPLE II

ANO-RECTAL PAD

The cream described in Example 1 was added to rectal pads and kept moist in a 10% glycerin solution in sealed packets. These premoistened pads impart cleansing and therapeutic properties to the perianal irritated skin and are also effective for relief of pain, soreness and burning associated with hemorrhoids and pruritus ani. Local anesthetics, such as 1.0% pramoxine hydrochloride or lidocaine may be added.

EXAMPLE III

SUPPOSITORY OINTMENTS

Suppositories have been formulated having the following compositions:

| Ingredient | Percentage by Weight |
| --- | --- |
| A. Water in Oil Base Ointment | |
| White Petroleum | 54 |
| Sorbitan Sesquioleate | 6 |
| Germaben II (Preservative) | Q.S. |
| Water | Balance |
| L-Glutathione | 0.2 |
| L-Selenomethionine | 0.05 |
| Superoxide Dismutase | 0.25 |
| Ascorbyl Palmitate | 1.25 |
| Alpha Tocopherol Acetate | 0.50 |

-continued

| Ingredient | Percentage by Weight |
| --- | --- |
| Retinyl Palmitate | 0.25 |
| Zinc pyrithione | 0.15 |
| B. Ointment | |
| White Petroleum | 15.0 |
| Mineral Oil | 15.0 |
| Spermaleti (Wax) | 5.0 |
| Sorbitan Monopalmitate | 5.0 |
| Tween-40 | 5.0 |
| (Polyoxyethelene Sorbitan Monopalmitate) | |
| L-Glutathione | 0.2 |
| L-Selenomethionine | 0.05 |
| Ascorbyl Palmitate | 1.0 |
| Retinyl Palmitate | 0.5 |
| Alpha Tocopherol Acetate | 0.75 |
| Zinc Acetate | 0.15 |
| Preservative (Germaben II) | 1.00 |
| Water | Balance |

EXAMPLE IV

HEMORRHOIDAL CREAM

A hemorrhoidal cream has been formulated having the following composition:

| Ingredient | Percentage by Weight |
| --- | --- |
| Amber Petroleum | Balance |
| Mineral Jelly | 48.00 |
| Lanolin Alcohol | 2.00 |
| Lanolin | 3.00 |
| Squalene Oil | 3.00 |
| Demineralized Water | 1.00 |
| L-Glutathione | 0.20 |
| L-Selenomethionine | 0.05 |
| *Superoxide Dismutase | 0.15 |
| *Vitamins A, C, E (liposome) | 3.00 |
| Japanese Green Tea | 0.50 |
| Thyme Oil | 0.10 |
| Preservative | |

Suppositories can be formulated with base ingredients such as waxes, oils, and fatty alcohols with characteristics of remaining in solid state at room temperatures and melting at body temperatures. The active ingredients of this invention with or without optional therapeutic ingredients, like hydrocortisone (1.0%), topical anesthetics like benzocaine (1.0 to 6.0%) or others as already listed may be prepared at appropriate pH values; for example pH5 liquid fatty alcohols, such as oleyl alcohol (range 45% to 65%) or solid higher fatty alcohols like cetyl or stearyl alcohol (30% to 50%). The base ingredients are well known in the art of this industry and some have been disclosed in U.S. Pat. Nos. 4,945,084 and 5,196,405 both by Packman and Oskman, the disclosures of which are incorporated by reference.

EXAMPLE V

SUPPOSITORY/STICK BASE

The following composition has been formulated for a Suppository/Stick Base:

| Ingredient | Percentage by Weight |
| --- | --- |
| Cetestearyl Palmitate | 17.0 |
| Lanolin USP | 17.0 |
| Paraffin Wax | 20.0 |
| Mineral Oil | Balance |

These ingredients are mixed together at 65° F.; as the mixture cools before hardening add mixture of the active ingredients:

| Ingredient | Percentage by Weight |
| --- | --- |
| L-Glutathione | 0.10 |
| L-Selenomethionine | 0.05 |
| *Superoxide Dismutase | 0.25 |
| *Vitamins A, C, E as liposome | 3.00 |
| or as tocopheryl acetate | 1.00 |
| magnesium ascorbyl phosphate | 2.00 |
| retinyl palmitate, retinyl palmitate | 0.50 |
| zinc oxide/zinc pyrithione | 0.15 |

*As liposomes: Biocell SOD, Brooks Industries and Rovisome ACE, R.I.T.A. Corporation or Crodasome AECL Corp.

*As liposomes: Biocell SOD, Brooks Industries and Rovisome ACE, R.l.T.A. Corporation or Crodasome AECL Corp.

The texture is smooth and it does not crystallize on storage. In other compositions the lanolin and cetestearyl palmitate may be replaced in toto or in part by spermceti, due to their similar characteristics.

The active ingredients in creams, lotions, ointments, sprays, pads, patches, enemas, foams and suppositories and others may be delivered in novel delivery vehicles such as micro-encapsulation in liposomes or glycospheres. Other delivery technologies include microsponges or the substitute cell membrane (Completech ™) which entrap the active ingredients for both protection and for slower release. Rectal foams can be prepared as topical aerosol compositions, again, as are well known in this industry with the express purpose of delivering the antioxidant complex of this application to reduce free radical damage in this ano-rectal inflammatory conditions, including inflammatory bowel diseases (ulcerative colitis, Crohns colitis, radiation proctitis and others).

I claim:

1. A method for ameliorating symptoms of hemorrhoids and other ano-rectal inflammation comprising topically applying to the rectum an amount of a composition of a topical carrier and a source of selenium and reduced glutathione in amounts effective to ameliorate said symptoms.

2. The method of claim 1 wherein said source of selenium is a seleno amino acid.

3. The method of claim 2 wherein said source of selenium is a member selected from the group consisting of selenomethionine and selenocysteine.

4. The method of claim 1 wherein said carrier is chosen to create in member selected from the group consisting of a cream, lotion, gel, ointment, suppository, enema, spray, foam and emulsion.

5. The method of claim 1 further comprising superoxide dismutase.

6. The method of claim 1 further comprising Japanese green tea.

7. The method of claim 1 further comprising a source of zinc.

8. The method of claim 7 wherein said source of zinc comprises a member selected from the group consisting of zinc oxide, mineral zinc glycopeptide and zinc pyrithione.

9. The method of claim 1 further comprising epidermal growth factor.

10. The method of claim 1 further comprising tissue respiratory factor.

11. The method of claim 1 further comprising one or more corticosteroids.

12. The method of claim 1 further comprising a member selected from the group consisting of anesthetics antiinflammatory, wound healing salts, vasoconstrictors, lubricants, astringents, antiseptics and antimicrobials, including antibiotics.

* * * * *